United States Patent [19]

Ekholm

[11] Patent Number: 4,659,222
[45] Date of Patent: Apr. 21, 1987

[54] MICROCUVETTE SET

[75] Inventor: Pertti Ekholm, Helsinki, Finland

[73] Assignee: Labsystems Oy, Helsinki, Finland

[21] Appl. No.: 653,242

[22] PCT Filed: Dec. 30, 1983

[86] PCT No.: PCT/FI83/00082

§ 371 Date: Sep. 5, 1984

§ 102(e) Date: Sep. 5, 1984

[87] PCT Pub. No.: WO84/02775

PCT Pub. Date: Jul. 19, 1984

[30] Foreign Application Priority Data

Jan. 7, 1983 [FI] Finland ................................ 830056

[51] Int. Cl.$^4$ ............................................. G01N 21/03
[52] U.S. Cl. ........................................ 356/244; 356/246
[58] Field of Search .............................. 356/244, 246

[56] References Cited

U.S. PATENT DOCUMENTS 4,055,470 10/1977 Sheaff et al. ...................... 356/244
4,319,841 3/1982 Suovaniemi et al. .............. 356/246
4,496,243 1/1985 Machida ............................ 356/244

Primary Examiner—Vincent P. McGraw
Attorney, Agent, or Firm—Hopgood, Calimafde, Kalil, Blaustein & Judlowe

[57] ABSTRACT

Microcuvette set which comprises several cuvettes (5) in a matrix form, arranged so as to be handled as one whole unit. The frame portion of the microcuvette set (1) consists of a preferably rectangular frame portion (2) designed so that two or more cuvette-set components (3) can be attached to it in the longitudinal or transverse direction one after the other. Each of the said cuvette-set components (3) consists of several cuvettes (5) disposed in a line or matrix form and connected to each other or attached together by means of a support plate (4), and the middle portion of the frame portion (2) is open at least within the area covered by the cuvettes (5) in the cuvette-set components (3). The microcuvette set (1) comprises a rectangular locking frame (6), open at its middle portion at least within the area corresponding to the frame portion (2), which locking frame is arranged so as to be attached to the top face of the frame portion (2), e.g., by means of a friction joint, so-called snap-in joint, or by means of any other joint suitable for the purpose. Thereby, the ends of the support plates (4) of the cuvette-set components (3) fitted into the frame portion (2) remain between the top face of the frame portion (2) and the locking frame (6).

4 Claims, 4 Drawing Figures

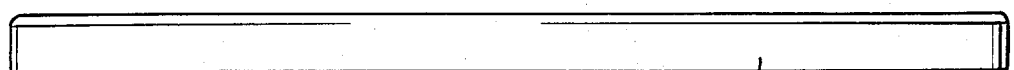
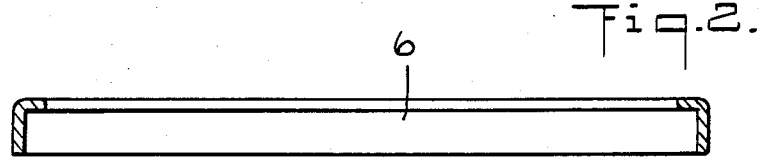
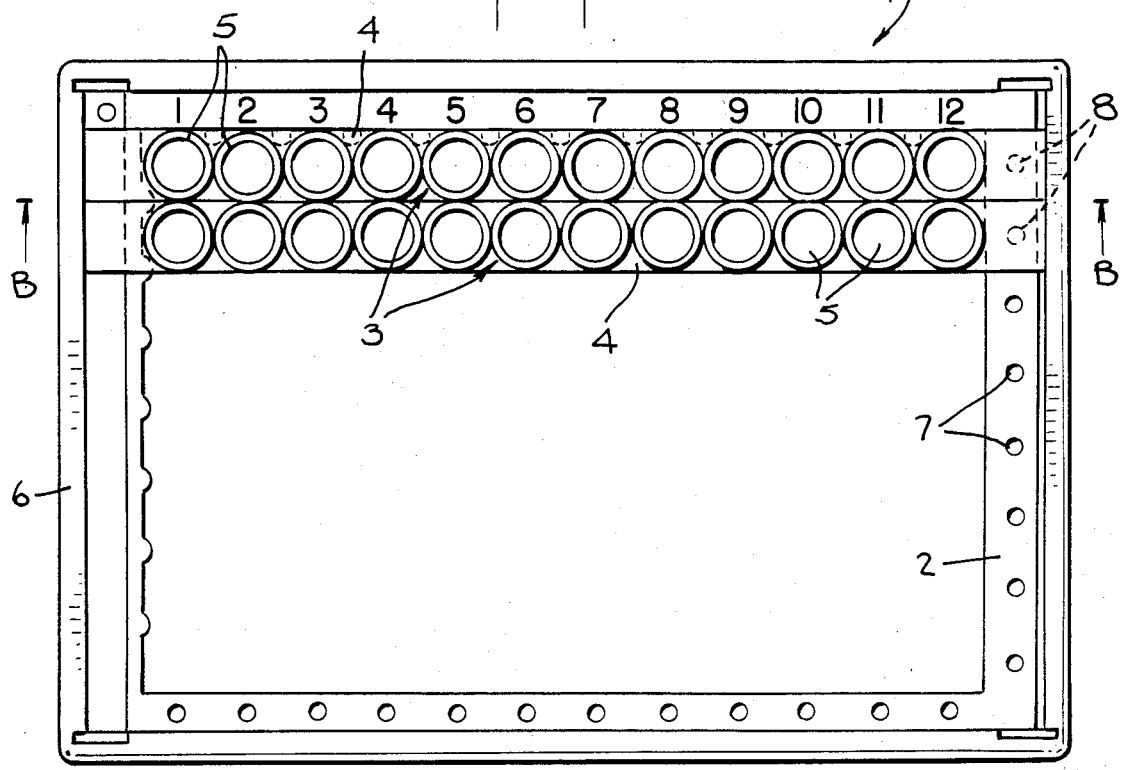
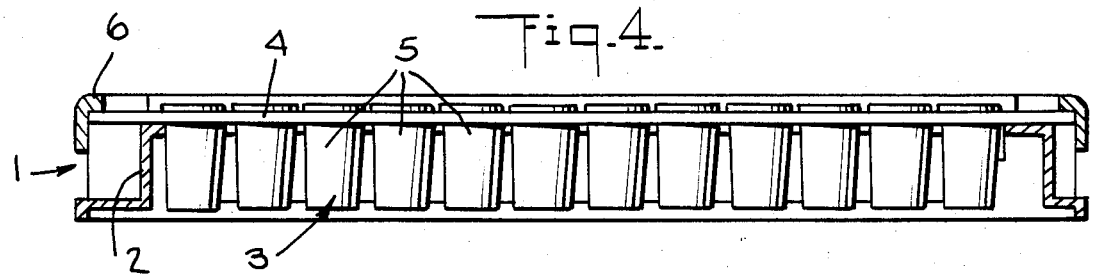

MICROCUVETTE SET

The present invention is concerned with a microcuvette set which comprises several cuvettes in a matrix form, arranged so as to be handled as one whole unit, whereat the frame portion of the microcuvette set consists of a preferably rectangular frame portion, designed so that two or more cuvette-set components can be attached to it in the longitudinal or transverse direction one after the other, whereat each of said cuvette-set components consists of several cuvettes disposed in a line or matrix form and connected to each other or attached together by means of a support plate, and the middle portion of the frame portion being open at least within the area covered by the cuvettes in the cuvette-set components.

The object of the invention is to provide an arrangement by means of which several cuvette-set components in the linear or matrix form can be made to remain in position in the frame portion. This is important in view of treatment of the microcuvette set, e.g., during washing, dosage of liquids, or performance of measurement operations.

According to the invention, the microcuvette set is provided with a particular locking frame, and the invention is mainly characterized in that the microcuvette set comprises a rectangular locking frame, open at its middle portion at least within the area corresponding to the frame portion, which locking frame is arranged so as to be attached to the top face of the frame portion, e.g., by means of a friction joint, so-called snap-in joint, or by means of any other joint suitable for the purpose, so that the ends of the support plate of the cuvette-set components fitted into the frame portion remain between the top face of the frame portion and the locking frame.

By means of the locking frame, all the different parts of the microcuvette set can be fixed to each other so that the microcuvette set can be handled as a single whole unit in any position whatsoever.

The invention comes out in more detail from the following description and from the attached drawing, wherein FIG. 1 is a side view of the locking frame, FIG. 2 shows a section along line A—A in FIG. 1, FIG. 3 shows the microcuvette set as viewed from above, and FIG. 4 is a sectional view along line B—B in FIG. 3.

The microcuvette set 1 consists of several parts. It comprises a rectangular frame portion 2, which is open in its middle portion and into which smaller units can be placed, which smaller units can be packed into this frame portion 2 one after the other. The size of the frame portion 2 is such that it is suitable for measurement in a photometer.

The number of cuvettes 5 in the cuvette-set components 3 is lower than 96, e.g. $4 \times 8 = 32$ or $6 \times 8 = 48$, $3 \times 8 = 24$, $1 \times 8 = 8$, or $1 \times 12 = 12$.

Two or more cuvette-set components 3 are arranged so as to be attached to the frame portion 2 one after the other, whereat each cuvette-set component 3 consists of several cuvettes 5 in a line or matrix form, the said cuvettes being connected to each other by means of a support plate 4.

In the exemplifying embodiment shown in FIGS. 3 and 4, cuvette-set components 3 of linear shape have been fitted into the frame portion 2. The top face of the frame portion 2 is provided with pins 7, as is shown in FIG. 3, and one end of the support plates 4 of the cuvette-set components 3 is provided with a hole 8, whereat the cuvette-set components 3 can be fitted into the frame portion 2 in one direction only.

The projections provided at the ends of the cuvette-set components 3, i.e, the ends of the support plates 4, remain on the top face of the frame portion 2, whereat the cuvette-set components 3 rest in support on the frame portion 2. The microcuvette set 1 additionally includes a rectangular locking frame 6, which is in its middle portion open at least within the area corresponding to the frame portion 2 and which is arranged so as to be attached to the top face of the frame portion 2, e.g., by means of a friction joint, a so-called snap-in joint, or in any other way suitable for the purpose. Thereby the ends of the support plates 4 of the cuvette-set components 3 fitted into the frame portion 2 remain between the top face of the frame portion 2 and the locking frame 6.

The locking frame 6 keeps the cuvette-set components tightly in position. The frame of the locking frame 6 is shaped in accordance with FIG. 2 so that it is very rigid at its long sides. This favours the keeping in position of the cuvette-set components. As the cross-sectional shape of the locking frame 6 is rectangular, owing to the rigidity obtained by means of the shape, it has been possible to minimize the consumption of material, and a low-weight locking frame 6 has been obtained. Also, the height of such a microcuvette set 1 is only about 1 mm higher than that of a conventional microtiter plate, so that the microcuvette set 1 can be used in apparatuses designed for microtiter plates (e.g. photometers). The locking frame 6 is advantageously made of a plastic material by means of the injection moulding technique.

What is claimed is:

1. A microcuvette unit including a plurality of cuvettes arranged in matrix form comprising in combination: a lower frame member defining a first open area about its center and support surfaces about its periphery, an upper locking frame member defining a second open area about its center corresponding to said first open area of said lower frame member, said upper locking frame member being constructed so that its periphery will engage the lower frame member when mounted thereupon to attach said locking frame member to said lower frame member, said locking frame member further defining locking surfaces arranged to be in facing relation with said support surfaces of said lower frame member when said frame members are lockingly attached one to the other, and a plurality of matrixed cuvettes arranged on support plates having at their edges coupling means, said coupling means being configured to cooperate with said support surfaces of said lower frame member so that said plurality of said support plates are disposed in a predetermined orientation when mounted on said lower frame member, whereby upon assembly of said plurality of cuvette matrices and frame members said coupling means of said matrices are lockingly engaged between said members and said first and second central open areas of said frame members are at least of sufficient area to accomodate said cuvettes so that each cuvette in said assembly is upwardly open.

2. The microcuvette unit according to claim 1, wherein said coupling means and support surfaces cooperate so that said plurality of matrices may each be lockingly engaged only in a single predetermined position.

3. The microcuvette unit according to claim 2, wherein said frame members and cuvette matrices are rectangular.

4. The microcuvette unit according to claim 3, wherein said lower frame member has a substantially continuous outer edge defining an angle of about 90 degrees at its outer portion and said upper frame member is provided with a lip corresponding to said angle constructed to fit thereabout and to be snappedly attached thereto.

* * * * *